(12) United States Patent
Amarasinghe

(10) Patent No.: US 9,636,476 B2
(45) Date of Patent: May 2, 2017

(54) HEADGEAR

(71) Applicant: ResMed Limited, Bella Vista, New South Wales (AU)

(72) Inventor: Amal Shirley Amarasinghe, West Pennant Hills (AU)

(73) Assignee: RESMED LIMITED, Bella Vista (AU)

( * ) Notice: Subject to any disclaimer, the term of this patent is extended or adjusted under 35 U.S.C. 154(b) by 853 days.

(21) Appl. No.: 13/938,807

(22) Filed: Jul. 10, 2013

(65) Prior Publication Data

US 2013/0319418 A1    Dec. 5, 2013

Related U.S. Application Data

(60) Continuation of application No. 12/805,787, filed on Aug. 19, 2010, now Pat. No. 8,505,538, which is a
(Continued)

(51) Int. Cl.
*A61M 16/06*    (2006.01)
*A62B 18/08*    (2006.01)
*A61M 25/02*    (2006.01)

(52) U.S. Cl.
CPC ....... *A61M 16/0683* (2013.01); *A62B 18/084* (2013.01); *A61M 2025/022* (2013.01);
(Continued)

(58) Field of Classification Search
None
See application file for complete search history.

(56) References Cited

U.S. PATENT DOCUMENTS

| RE20,211 E | 12/1936 | Motsinger |
|---|---|---|
| 4,099,524 A | 7/1978 | Cueman et al. |

(Continued)

FOREIGN PATENT DOCUMENTS

| EP | 0 747 078 A2 | 12/1996 |
|---|---|---|
| EP | 1 020 201 A2 | 7/2000 |

(Continued)

OTHER PUBLICATIONS

European communication corresponding EP Appln No. 10 183 527.8-1662, mailed Jun. 13, 2013, 3 pages.
(Continued)

*Primary Examiner* — Rachel Young
(74) *Attorney, Agent, or Firm* — Nixon & Vanderhye, P.C.

(57) ABSTRACT

A mask assembly suitable for the treatment of sleep disordered breathing, comprising: a mask to provide pressurized air to a patient; upper and lower slot features located on each side of the mask; a headgear assembly, comprising: a back portion; a pair of upper straps provided to the back portion, each upper strap having a loop portion and a hook portion at a free end thereof for releasably attaching to the loop portion; a pair of lower straps extending away from the back portion, each lower strap having a loop portion and a hook portion at a free end thereof for releasably attaching to the loop portion; and a connection region of each loop portion of each strap, the connection region being adapted to receive a respective hook portion, the connection region being wider than each respective hook portion along each respective hook portion's entire length.

55 Claims, 7 Drawing Sheets

Related U.S. Application Data division of application No. 11/701,362, filed on Feb. 2, 2007, now Pat. No. 7,802,573, which is a continuation of application No. 10/433,779, filed as application No. PCT/AU01/01607 on Dec. 12, 2001, now Pat. No. 7,188,620.

(60) Provisional application No. 60/254,537, filed on Dec. 12, 2000.

(52) U.S. Cl.
CPC  *A61M 2025/026* (2013.01); *Y10T 428/24008* (2015.01); *Y10T 428/24017* (2015.01)

(56) References Cited

U.S. PATENT DOCUMENTS

| | | |
|---|---|---|
| 4,367,735 A | 1/1983 | Dali et al. |
| 4,437,462 A | 3/1984 | Piljay et al. |
| 4,640,269 A | 2/1987 | Goins |
| 4,671,271 A | 6/1987 | Bishop et al. |
| 5,117,819 A | 6/1992 | Servidio et al. |
| D334,633 S | 4/1993 | Rudolph |
| 5,237,988 A | 8/1993 | McNeese |
| 5,265,595 A | 11/1993 | Rudolph |
| 5,284,469 A | 2/1994 | Jasen et al. |
| 5,481,763 A | 1/1996 | Brostrom et al. |
| 5,488,948 A | 2/1996 | Dubruille et al. |
| 5,490,504 A | 2/1996 | Vrona et al. |
| 5,517,986 A | 5/1996 | Starr et al. |
| 5,529,062 A | 6/1996 | Byrd et al. |
| 5,542,128 A | 8/1996 | Lomas et al. |
| 5,560,354 A | 10/1996 | Berthon-Jones et al. |
| D383,204 S | 9/1997 | Lomas |
| 5,806,516 A | 9/1998 | Beattie |
| 5,840,050 A | 11/1998 | Lerman |
| 5,921,239 A | 7/1999 | McCall et al. |
| 5,924,421 A | 7/1999 | Rosbrook et al. |
| 5,946,735 A | 9/1999 | Bayes |
| 5,950,248 A | 9/1999 | Kawashima et al. |
| 6,016,807 A | 1/2000 | Lodge |
| 6,062,222 A | 5/2000 | Lewis et al. |
| 6,067,985 A | 5/2000 | Islava |
| 6,105,573 A | 8/2000 | Delaplane et al. |
| 6,119,693 A | 9/2000 | Kwok et al. |
| D433,127 S | 10/2000 | Gazzara |
| 6,269,814 B1 | 8/2001 | Blaszczykiewicz et al. |
| 6,422,238 B1 | 7/2002 | Lithgow |
| 6,470,886 B1 | 10/2002 | Jestrabek-Hart |
| 6,494,207 B1 | 12/2002 | Kwok |
| 6,591,837 B1 | 7/2003 | Byram |
| 6,732,733 B1 | 5/2004 | Brostrom et al. |
| 6,772,760 B2 | 8/2004 | Frater et al. |
| 7,188,620 B2 | 3/2007 | Amarasinghe |
| 7,219,669 B1 | 5/2007 | Lovell et al. |
| 2004/0067333 A1 | 4/2004 | Amarasinghe |
| 2004/0112377 A1 | 6/2004 | Amarasinghe et al. |
| 2007/0169777 A1 | 7/2007 | Amarasinghe |
| 2010/0319688 A1 | 12/2010 | Amarasinghe |

FOREIGN PATENT DOCUMENTS

| | | |
|---|---|---|
| EP | 1 057 494 A2 | 12/2000 |
| FR | 2 618 340 A | 1/1989 |
| GB | 2 247 396 A | 3/1992 |
| WO | WO 96/25983 | 8/1996 |
| WO | WO 96/28207 | 9/1996 |
| WO | 97/32493 | 9/1997 |
| WO | 98/48878 A2 | 11/1998 |

OTHER PUBLICATIONS

European Search Report for corresponding EP Appln No. 10183627, mailed Mar. 17, 2011, 12 pages.
Extended European Search Report in EP 10 18 5034 dated Feb. 22, 2011 (6 pages).
Extended European Search Report in EP 10 18 5039 dated Feb. 16, 2011.
Supplementary European Search Report for EP 01270356.7 mailed Feb. 3, 2006, 3 pages.
European Office Action for corresponding EP Application No. 01 270 356.7, mailed Jun. 11, 2007, 3 pages.
U.S. Appl. No. 60/293,992, filed May 30, 2001, Frater et al.
U.S. Appl. No. 60/219,618, filed Jul. 21, 2000, Frater et al.
U.S. Appl. No. 60/213,251, filed Jun. 22, 2000, Frater et al.
Opposition Against EP Patent 1349602 issued in related EP Application No. 01 27 0356.7, "Facts and Arguments" dated Dec. 10, 2013, with English translation, 28 pages.
Opposition Against EP Patent 1349602 issued in related EP Application No. 01 27 0356.7, "Opponent's Brief" dated Dec. 17, 2013, with English translation, 2 pages.
Opposition Against EP Patent 1349602 issued in related EP Application No. 01 27 0356.7, "Opponent's Supplementary Submissions" dated Feb. 19, 2014, with English translation, 9 pages.
Communication Pursuant to Article 94(3) EPC issued in related European Application No. 10 185 034.5 dated Sep. 16, 2015, 4 pages.
European Communication under Rule 71(3) EPC corresponding EP Appln No. 01 270 356.7-1662, dated Jul. 10, 2013, 7 pages.

HEADGEAR

CROSS-REFERENCES TO RELATED APPLICATIONS

This is a continuation of U.S. application Ser. No. 12/805,787, filed Aug. 19, 2010, now U.S. Pat. No. 8,505,538, which is a division of U.S. application Ser. No. 11/701,362, filed Feb. 2, 2007, now U.S. Pat. No. 7,802,573, which is a continuation of U.S. application Ser. No. 10/433,779, filed Nov. 13, 2003, now U.S. Pat. No. 7,188,620, which is a national phase of International Application No. PCT/AU01/01607, filed Dec. 12, 2001, which claims the benefit of U.S. Provisional Application No. 60/254,537, filed Dec. 12, 2000, each incorporated herein by reference in its entirety.

BACKGROUND OF THE INVENTION

Field of the Invention

The invention relates to headgear for use with a mask suitable for the delivery of non-invasive positive pressure ventilation and for nasal CPAP treatment of sleep disordered breathing conditions such as obstructive sleep apnea.

Description of Related Art

Obstructive Sleep Apnea (OSA) is a disease characterised by excessive daytime sleepiness, loud snoring and daytime irritability. Other effects of OSA can include depression, high blood pressure, serious heart conditions, sexual problems, memory lapses, intellectual deterioration and morning headaches.

The treatment of OSA by the application of nasal Continuous Positive Airway Pressure (CPAP) was invented by Sullivan and is described in U.S. Pat. No. 4,944,310 (Sullivan, assigned to ResMed Limited). The technique involves the application of a flow of pressurised breathable gas (typically room air) to either the nose or nose and mouth of a patient while they sleep. The technique is said to "splint" open the airways. Typical treatment pressures are in the range of 3 to 20 cmH2O. Flows are up to approximately 200 L/min. The flow of pressurised air is produced by a blower and delivered to the patient via a patient interface. The blower and patient interface are joined by a conduit. Whilst there are other techniques for the treatment of OSA, such as surgery, the use of CPAP has become the "gold" standard.

For a particular patient, the pressure which is needed to maintain open airways can vary throughout the night and vary on different nights. U.S. Pat. No. 5,245,995 (Sullivan and Lynch, assigned to ResMed Limited) describes a method and device for varying the pressure in accordance with indications. For example, if the patient starts to snore, the pressure automatically increases, whilst in the absence of snoring, the pressure automatically decreases.

Non-Invasive Positive Pressure Ventilation (NIPPV) is another form of treatment for breathing disorders. In its most basic form, it involves a relatively higher pressure of gas being provided in the patient mask during the inspiratory phase of respiration and a relatively lower pressure or atmospheric pressure being provided in the patient mask during the expiratory phase of respiration. Typical treatment pressures are in the range of 3 to 30 cmH, 0.

In other NIPPV modes, the pressure can be made to vary in a complex manner throughout the respiratory cycle. For example, the pressure at the mask during inspiration or expiration can be varied through the period of treatment, as disclosed in international PCT patent application no. PCT/AU97/00631 (Berthon-Jones, assigned to ResMed Limited).

In this specification, any reference to CPAP is to be understood as embracing all of the above-described forms of ventilatory treatment or assistance.

One of the earliest patient interfaces for providing CPAP treatment was constructed to include a fibreglass model of the patient's nose. The model was adhered to the patient's nose each night and removed each morning. An advantage of this patient interface included the customised fit, which assisted in a good seal between the patient interface and the patient's airways. However, the use of adhesive to secure the mask was inconvenient and not desirable.

Another suitable patient interface is described in U.S. Pat. No. 5,243,971 (Sullivan and Bruderer, assigned to the University of Sydney), entitled "Nasal Mask for CPAP having Ballooning/Moulding Seal with Wearer's Nose and Facial Contours". This patent describes a nasal mask 25 with a soft face-contacting portion, and a rigid shell. The mask 25 is held in position using headgear. The headgear is attached to the mask 25 and passes around the back of the wearer's head. The patent depicts two sets of straps in the headgear. The first set comprised a pair of straps passing from the forehead region to the back of the head. The second set comprised a pair of straps passing from the nasal region of the mask to the back of the head. The mask 25 also includes a forehead support 29 and an elbow 18, as shown in FIG. 8.

Another known patient interface is the MIRAGE® nasal mask (by ResMed Ltd), which is shown in FIG. 7. This nasal mask 14 includes a pair of headgear attachment points in the nasal region of the mask shell and a forehead support 10 that includes another pair of headgear attachment points 18, 20. The headgear 16 includes a single piece of a soft, flexible composite fabric with a generally triangular back portion and four straps. The four straps include a pair of upper straps and a pair of lower straps connecting to the headgear attachment points on the forehead support and nasal mask shell respectively. At the end of each strap is secured a piece of hook material, which, in use, passes through a headgear attachment point and fastens on corresponding loop material on the strap. The generally triangular back portion engages the skull in the region of the occiput. The fabric stretches under a load. The base of the triangle is positioned near and generally in line with the upper straps. Each strap is approximately 2 cm wide and approximately 3 mm thick. The fabric is a composite of three layers. The inner layer, closest to the patient's head, is made from nylon. The middle layer is made from neoprene. The outer layer is made from loop material, suitable for engaging with hook fastening material such as Velcro™. The upper straps have an approximate length of 19 cm, from the end to the closest corner of the triangle, whilst the lower straps have an approximate length of 26 cm. Including the triangle, the upper and lower straps each have an approximate total length of 60.5 cm. The triangular back portion is an approximate isosceles triangle, with a base of approximately 13.5 cm and sides of approximately 9 cm.

Some patients open their mouths during sleep, which means that they may not receive the benefit of CPAP due to mouth leaks. Various solutions have been proposed for this problem. One solution is taught in U.S. Pat. No. 6,123,082 (Berthon-Jones, assigned to ResMed Limited), whereby the lips are held closed. Another solution is to use a mask that covers both the nose and mouth of the patient. An example of a mouth and nasal mask is described in U.S. Pat. No. 5,560,354 (Berthon-Jones, Calluaud, Lynch & Hely, assigned to ResMed Limited).

Another suitable mask system is the MIRAGE® full-face mask (by assignee ResMed Limited). The MIRAGE® full-face mask and headgear is illustrated in FIGS. 1, 2 and 3. Suitable headgear (102) for this mask (100) is constructed from a composite material of nylon, neoprene and loop material. The headgear similarly comprises a pair of upper (104) and a pair of lower straps (106) and a generally triangular back portion (108). The upper strap has a total length of approximately 610 mm as shown in FIG. 3. The straps have an approximate width of 25 mm, however, the upper strap has an approximate width of 19 mm. The triangular region has a base of approximately 15.5 cm and two equal sides of approximately 11 cm. The upper and lower straps are approximately 192 mm apart. In addition, the headgear includes a quick release mechanism (110), as described in the pending U.S. patent application Ser. No. 09/482,718 (Lithgow, assigned to ResMed Limited). The quick release mechanism provides a "rip-chord" that can be pulled upon to separate the headgear and remove the mask in an emergency. When the headgear is positioned on the patient's head, the quick-release mechanism is situated at the back of the head and the chord runs through loops towards the front of the mask system.

Patient interface arrangements include nasal masks, nose and mouth masks, nasal prongs and nasal pillows. In all forms of patient interface used with CPAP for treating sleep disordered breathing, there is a need to counterbalance the force of the pressurised air and to correctly position the interface. Since the patient must sleep with this interface, it is important that it be comfortable. From the manufacturing and distribution channel perspectives, it is advantageous if one size of headgear fits a large range of head shapes and sizes.

It should be noted that while there are many mask and headgear arrangements available for ventilators, respirators, aviator masks and other breathing apparatus, in general, these may not be suitable for use in the treatment of sleep disordered breathing because they are not sufficiently comfortable to allow the patient to sleep.

The present invention is directed towards providing headgear for holding and securing a mask for use in the treatment of sleep disordered breathing which improves patient comfort, is long lasting and fits a wide range of head shapes and sizes.

BRIEF SUMMARY OF THE INVENTION

The invention provides headgear for securing and positioning a mask suitable for the treatment of sleep disordered breathing with the following advantageous combination of features:
(i) Constructed from a composite including polyurethane foam
(ii) Relatively narrow strap ends,
(iii) Displaced lower strap,
(iv) A quick release mechanism near the front of the face; and
(v) Additional attached components to alter the elasticity and stiffness of the straps.

DETAILED DESCRIPTION OF THE INVENTION

Figure 1:
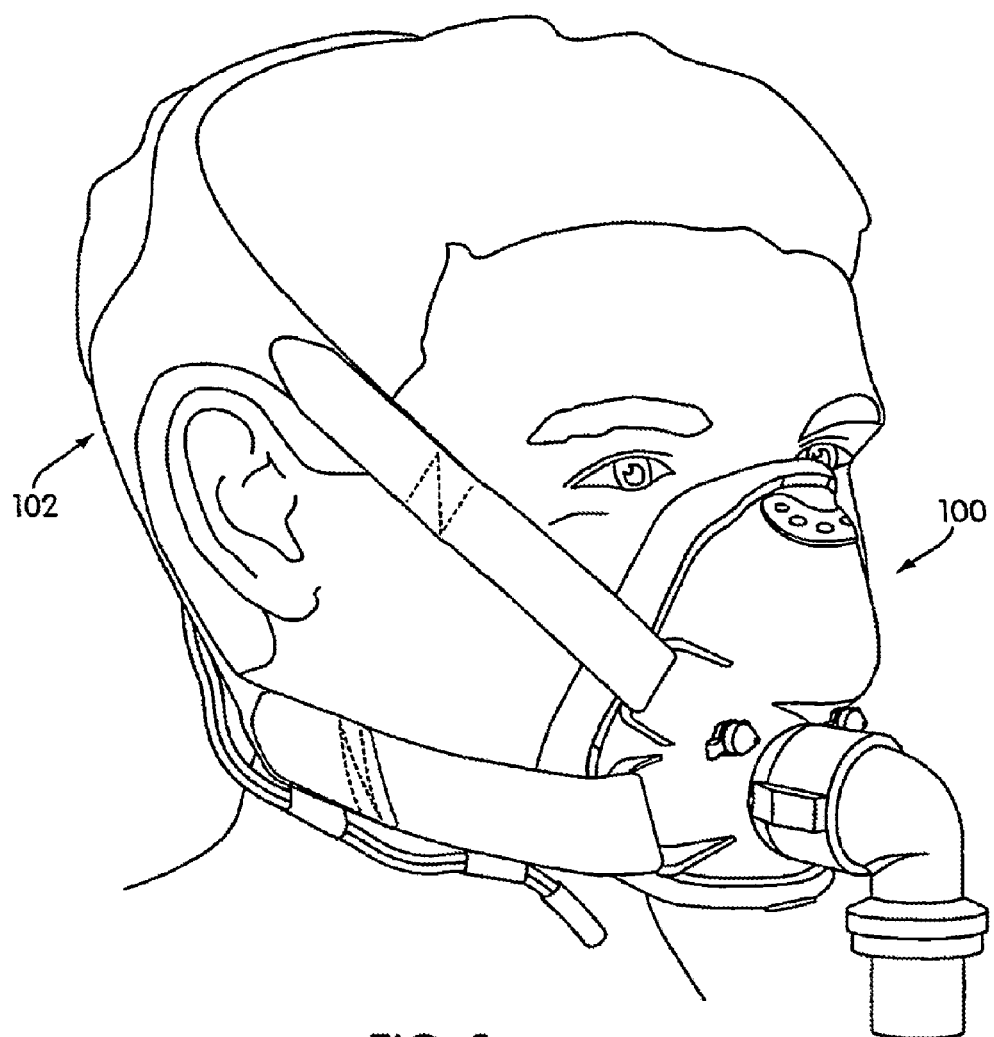
FIG. 1 shows a front three-quarter view of a MIRAGE® full-face mask and prior art headgear system in position on a patient's head.
Figure 2:
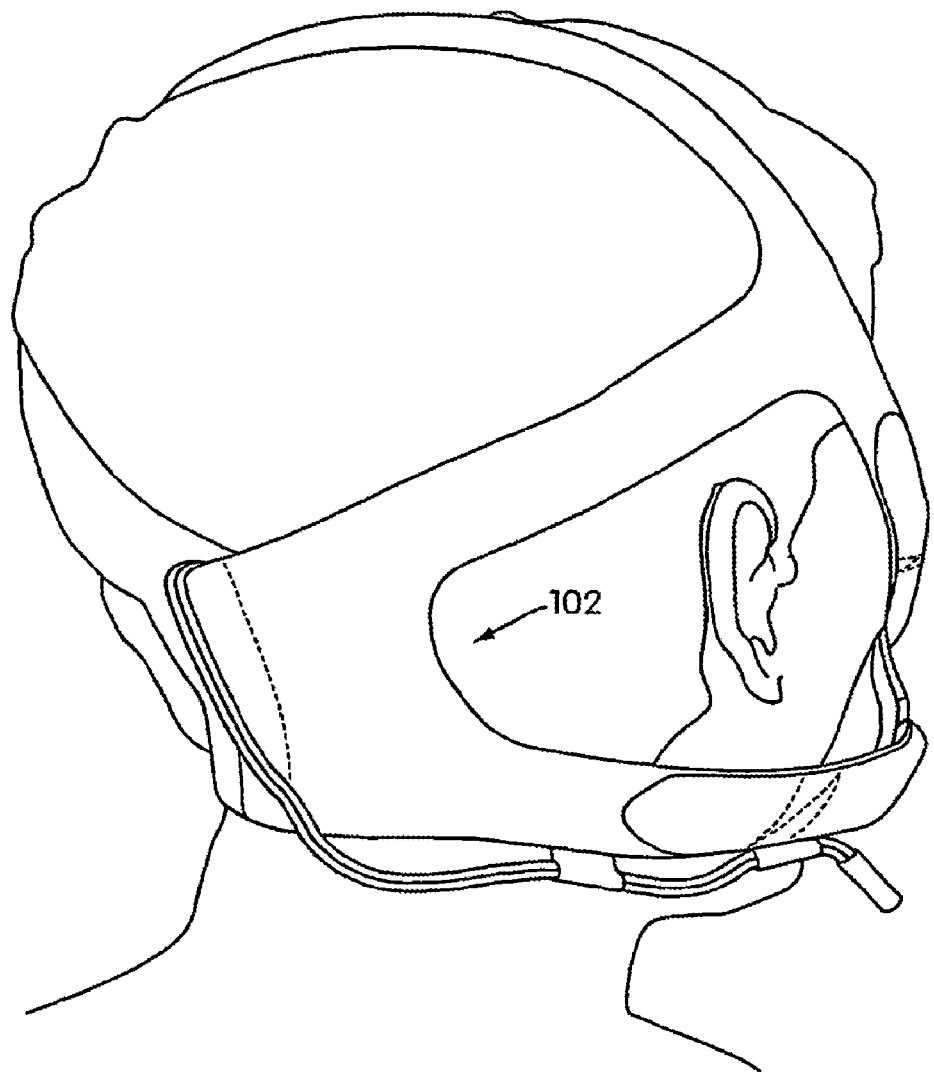
FIG. 2 shows a rear three-quarter view of a MIRAGE® full-face mask and prior art headgear system on a patient's head.
Figure 3:
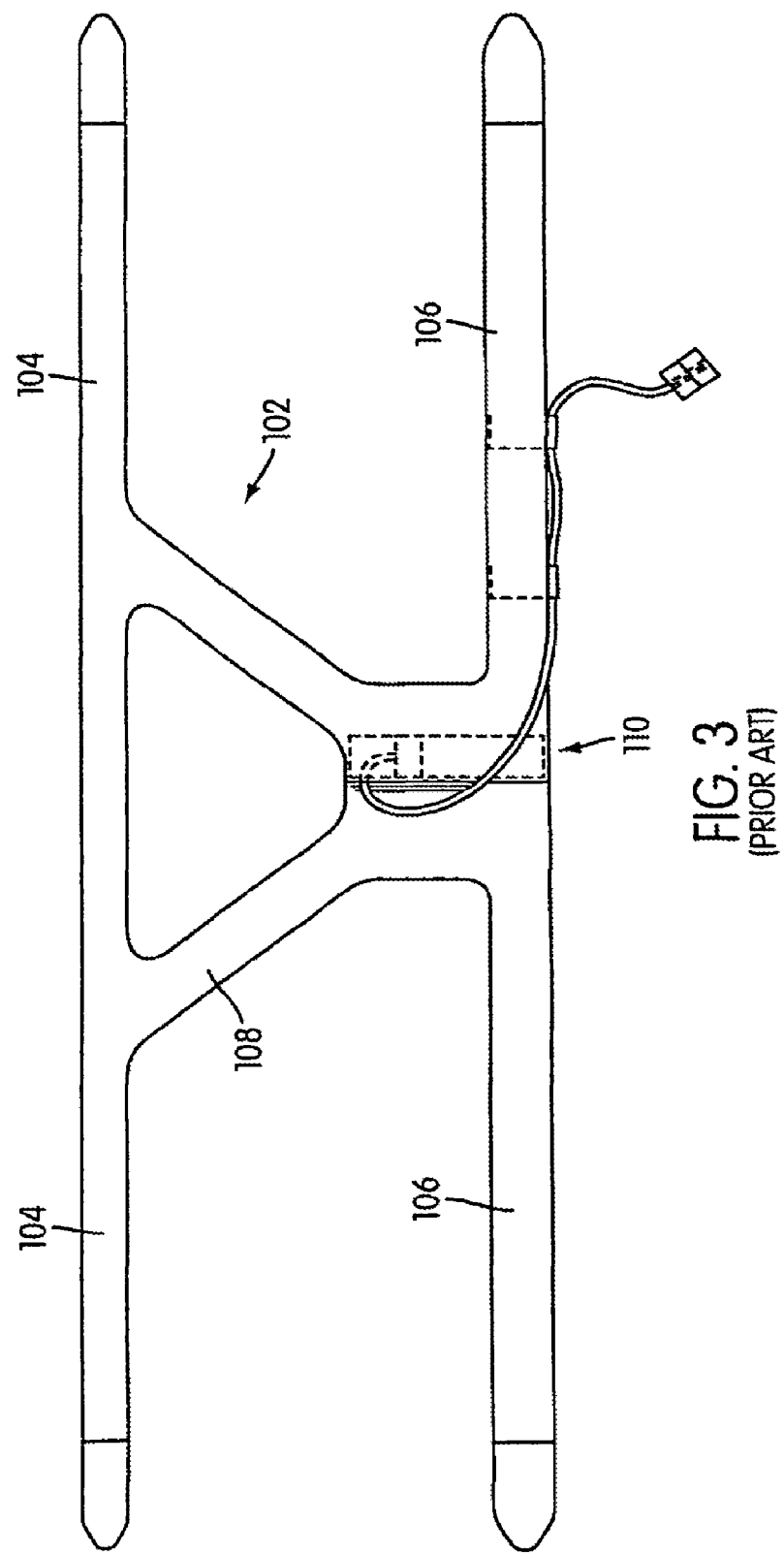
FIG. 3 shows a view of prior art full-face mask headgear laid flat.

The invention provides headgear (10) for securing and positioning a mask suitable for the treatment of sleep disordered breathing.
(i) Material The headgear is constructed from a composite of polyurethane foam, loop material and hook material whose shape includes a pair of upper straps (20) and lower straps (30) and a generally triangular back portion (40). A piece of hook material (22) is attached to the end of each of the four straps so that the straps may be secured to the attachment points on the mask. The end includes a main body (23) and a tapered free end portion (25).

The composite has three layers. The first layer, which in use is positioned against the head of the patient, is constructed from polyester or nylon fabric. The second, middle layer is constructed from an hypoallergenic breathable polyurethane foam. The third layer is constructed from loop material. A suitable material for constructing the composite is BREATH-O-PRENE® manufactured by ACCUMED, New York, United States of America. The total thickness of the composite is approximately 2 mm. The upper and lower pairs of straps are approximately 150 mm apart when laid flat. The upper and lower straps have an approximate total length (from the left side to the right side) of 610 mm.

The generally triangular back portion (40) of the headgear (10) is constructed and arranged to engage generally with the occiput of the patient's head in use. In use, the base of the triangle is positioned at the crown of the head, while the apex of the triangle lies generally just above the point of contact between the skull and the muscles of the neck.
(ii) Relatively Narrow Strap Ends The headgear of the present invention is configured to minimize the discomfort associated with the use of hook material. In prior art headgear, that discomfort can arise where the hook material may be in contact with the patient's skin, say the cheek or neck regions, for extended periods of time. That undesirable contact will occur where the hook material, to some extent is not entirely located on the receiving loop material, but lies tangential to the loop material, and to some extent extends beyond the loop material and comes in contact with the patient's skin, either continuously while the headgear is in use or when it is compressed against the skin, as can occur when the patient head changes position during the sleep period.

Figure 4:
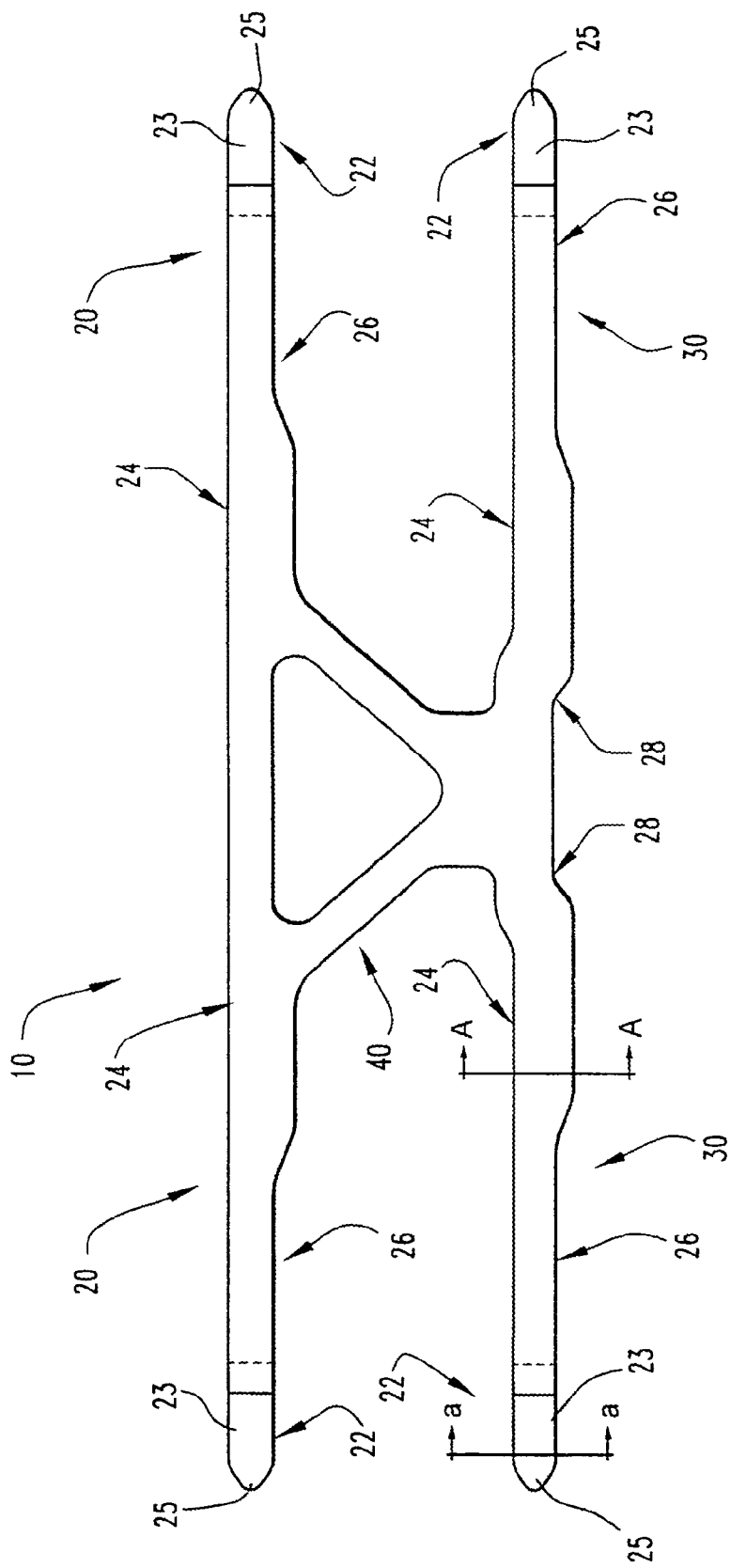
FIG. 4 shows a view of headgear according to an embodiment of the present invention.

As shown in FIG. 4, the width of each lower strap is constant for approximately half their length, forming a relatively wide portion (24), and then over a relatively short distance, changes to a narrower width for the remaining half of their length, forming a relatively narrow portion (26), terminating at the point where the hook material (22) is joined to the composite material. A characteristic of this configuration is that the point of contact where the hook material detachably binds with the strap loop material is positioned on the wide portion (24) and is wider by approximately 1 cm than the width of the engaging hook material. By adopting this configuration, the target region for binding is relatively greater in area than is the case with prior art. Prior art headgear includes a tapered end hook section that is of narrower width than that of the intended contact loop section of the strap. However, the prior art hook section tapered end is less than one half the length of the hook section, that is, it does not represent the majority of the length of the hook section nor does its length represent the majority of the length of the intended corresponding contact loop section (i.e., the maximum extent of the loop section covered by the hook section).

In contrast to the prior art, with the present invention the attachment of the hook material is facilitated, as relatively less precision is required in the placement of the hook section to achieve binding. This reduced dependence on precision is of advantage to all persons using the headgear and is of particular benefit to the user that may be trying to fit the headgear in a home environment and where it is not possible to directly sight the headgear components they are manipulating. Furthermore, compared to the prior art (where the hook material and the target region are of substantially the same width), this configuration reduces the chance of exposing some of the hook material to interfere with the wearer, causing discomfort and possibly skin irritation or abrasion.

(iii) Displaced Lower Strap

A length of each of the left and right lower straps is displaced vertically lower by approximately 1 cm (28). By adopting this configuration, it is possible to optimize the design of the base of the back portion so as to achieve the desired security of attachment but avoid compromising comfort in a situation where the lowest point of the headgear in the occiput region is extended to a position that is lower than is otherwise required in order to achieve a sufficiently lowest strap point. This approach avoids the prior art problem of having the headgear rear portion extending beyond what would otherwise be required and thereby engaging the sensitive area below the occipital lobe.

(iv) Quick Release Mechanism

Figure 5:
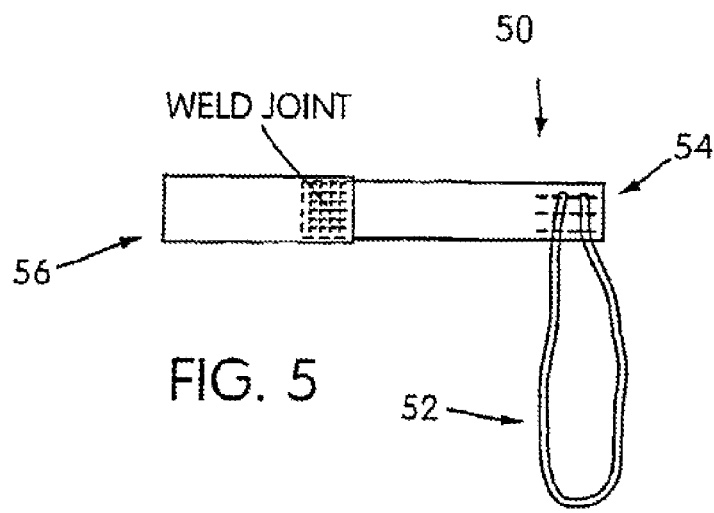
FIG. 5 shows a view of the quick release mechanism according to the present invention.

Preferably the headgear of the present invention includes a quick release mechanism (50) (see FIG. 5), and this is especially so when the headgear is intended to be used with a mask that covers the patient's nose and mouth.

The quick-release mechanism (50) suitable for incorporation into the preferred embodiment is constructed from a sub-assembly of three components: (i) a release loop of a cord material (52), (ii) a generally rectangular length of hook material (54), and (iii) a generally rectangular length of a composite fabric (56) which can bind to the hook material, as discussed above. The sub-assembly is generally rectangular in shape and in use forms an extension of one of the lower straps. Preferably the loop cord is constructed from braided cord about 17 cm long. The cord loop (52) is sewn to one end of the length of hook material (54). The hook material (54) and composite fabric (56) are joined at the other end of the hook material (54), preferably via a weld joint. In use, the end of the hook material (54), to which is connected the loop cord (52), is secured, using the hook and loop mechanism, to the end of a modified lower strap which, in contrast to the lower straps (30) shown in FIG. 4, does not contain hook material. The other end (56) of the quick release mechanism (50) is free to be connected to a headgear attachment point on the mask shell and releasably attached to an exposed portion of the hook material (54). If it is desired to use the quick-release mechanism (50), it is convenient for the patient to pull down on the loop of braided cord (52), thereby disengaging the lower strap from the mask shell and allowing the mask to then be readily removed from the patient's face. A quick-release mechanism of this configuration may be used on headgear that is fabricated of materials and in configurations that are different to those of the type described above and as such is an invention in its own right.

(v) Altering the Stiffness and Extensibility

Figure 6A:
FIG. 6A shows a view of a mask headgear strap in accordance with the present invention laid flat.
Figure 6B:
FIG. 6B shows a view of a mask headgear strap in accordance with the present invention laid flat.
Figure 7:
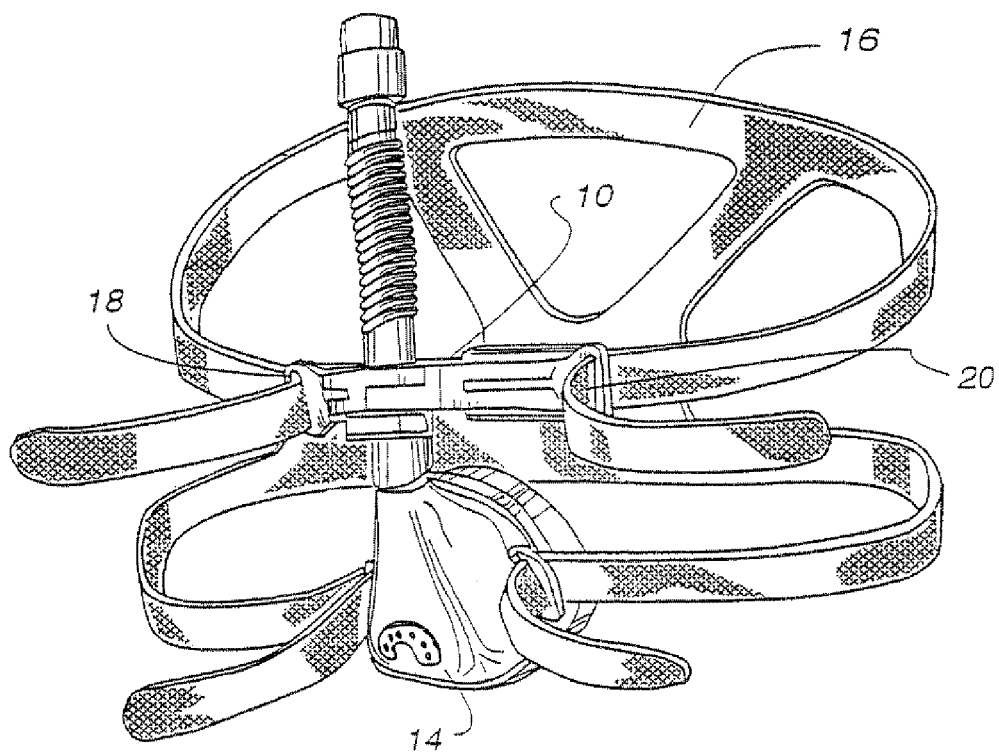
FIG. 7 shows a front perspective view of a prior art mask.
Figure 8:
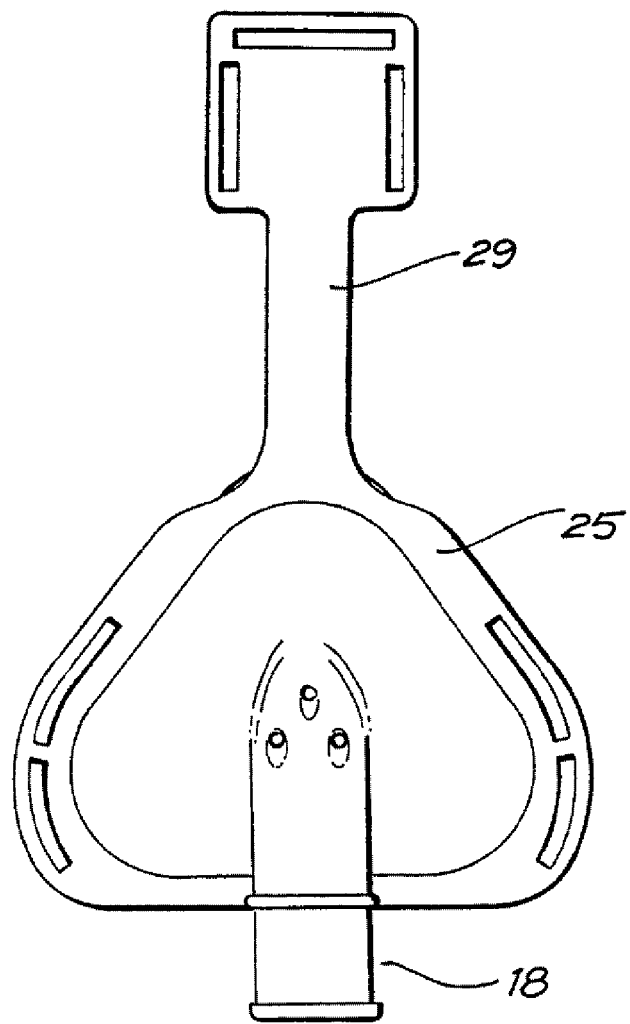
FIG. 8 shows a front view of a prior art mask.

In one form of the invention, the extensibility of the straps can be altered by attaching lengths of generally inextensible material (62) such as cotton or silk to the straps, as shown in FIG. 6B. The effect of this arrangement is to make the headgear less extensible along the length of the straps than in a vertical direction. In a preferred embodiment, lengths of cotton are sewn to the straps.

In another form of the invention, the stiffness of the straps can be altered by attaching stiffening material (64) to the top and bottom edge of the straps, as shown in FIG. 6A. Alternatively, or in addition, the strap may be stiffened by any other suitable means including by adding stitching as lines, in a crisscross pattern, or both. This makes the headgear less "floppy" and more convenient to put on the head of a wearer.

In another form of the invention, the headgear is constructed from an anisotropic material that is more extensible in a first direction than in a direction at an angle of 90 degrees to the first direction. This enables the headgear to be cut from a single piece of composite material and yet have different extensibilities in different directions. Preferably, the headgear will be more extensible in a vertical direction than in a horizontal direction. Hence the upper and lower straps will be less extensible in a direction along their length than in a direction along their width. This means that the back portion of the headgear can be more extensible in a direction from the base of the skull to the crown, than in a direction at right angles to that direction.

What is claimed is:

1. A mask assembly suitable for the treatment of sleep disordered breathing, comprising:

a mask configured to provide pressurized air to a patient in the range of 3 to 20 cmH2O throughout the patient's respiratory cycle, the mask including a soft, face-contacting portion and a rigid shell; a pair of upper headgear attachment points; a pair of lower headgear attachment points; and a headgear assembly configured to hold the mask in position on the patient's face during treatment, comprising:

a top portion;

a bottom portion;

a pair of side portions;

an opening defined by the top portion, the bottom portion, and the pair of side portions;

a pair of elongated upper straps extending away from opposing sides of the top portion;

a pair of elongated lower straps extending away from opposing sides of the bottom portion; and a transition between the bottom portion and the pair of elongated lower straps, the transition being angled downwardly relative to the bottom portion such that a lower edge of each of the pair of elongated lower straps is positioned lower than a lower edge of the bottom portion in use, wherein each of the pair of elongated upper straps and each of the pair of elongated lower straps include a loop material positioned along an external surface thereof and a hook material configured to releasably attach to the loop material to attach the pair of elongated upper straps and the pair of elongated lower straps to the mask, wherein the pair of elongated upper straps are dimensioned to extend above the patient's ears in use, wherein the pair of elongated lower straps are dimensioned to extend below the patient's ears and across the patient's facial skin, wherein the loop material of each of the pair of elongated upper straps and each of the pair of elongated lower straps includes a connection region adapted to attach to the hook material of a corresponding strap, the connection region being wider than the hook material such that when the hook material is attached to the loop material, in use, the loop material at each connection region is configured to shield the patient's facial skin from contact with the hook material, wherein a leading end of each of the pair of elongated upper straps is configured to pass through a corresponding one of the pair of upper headgear attachment points and be doubled-back on itself to attach the hook material to the loop material to secure the headgear assembly to the mask, wherein the loop material of each of the pair of elongated lower straps is configured to pass through a corresponding one of the pair of lower headgear attachment points and doubled-back on itself to attach the hook material to the loop material to secure the headgear assembly to the mask, and wherein each connection region of each elongated lower strap is adapted to engage the patient's facial skin.

2. The mask assembly of claim 1, wherein the pair of elongated upper straps and the pair of elongated lower straps consist essentially of four straps.

3. The mask assembly of claim 1, wherein the top portion is adapted to engage the crown of the patient's head.

4. The mask assembly of claim 1, wherein the bottom portion is dimensioned and configured so as to avoid engaging the patient's head below the occipital lobe in use.

5. The mask assembly of claim 1, wherein the top portion is dimensioned and configured to extend across the top of the patient's head from a first lateral side to a second lateral side of the patient's head in use.

6. The mask assembly of claim 1, wherein a thickness of each of the pair of elongated upper straps and the pair of elongated lower straps is approximately 2 mm.

7. The mask assembly of claim 1, wherein each of the pair of elongated upper straps and each of the pair of elongated lower straps is formed of a composite having a first layer to be positioned against the patient's head, a second, middle layer constructed from foam, and a third layer including the loop material.

8. The mask assembly of claim 1, further comprising vent holes adapted to vent exhaled air from the mask.

9. The mask assembly of claim 1, further comprising at least one port in communication with an interior of the mask.

10. The mask assembly of claim 1, further comprising an elbow connected to the mask, the elbow adapted to deliver pressurized gas to an interior of the mask.

11. The mask assembly of claim 1, wherein the mask is a full face mask.

12. The mask assembly of claim 1, wherein the mask is a nasal mask.

13. The mask assembly of claim 1, wherein the opening is arranged to receive the occiput of the patient's head.

14. The mask assembly of claim 1, wherein the headgear assembly is formed without reinforcement or stiffeners.

15. The mask assembly of claim 1, wherein the pair of elongated upper straps and/or the pair of elongated lower straps are dimensioned such that each connection region is located proximal to the patient's cheeks.

16. The mask assembly of claim 1, wherein the pair of elongated upper straps and the pair of elongated lower straps consist essentially of four straps, wherein the top portion is dimensioned and configured to extend across the top of the patient's head from a first lateral side to a second lateral side of the patient's head in use, wherein a thickness of each of the pair of elongated upper straps and the pair of elongated lower straps is approximately 2 mm, wherein the pair of elongated upper straps and the pair of elongated lower straps are configured such that the elongated upper strap and the elongated lower strap on each lateral side of the headgear assembly are substantially parallel when the headgear assembly is laid flat, wherein each of the pair of elongated upper straps and each of the pair of elongated lower straps is formed of a composite having a first layer to be positioned against the patient's head, a second, middle layer constructed from foam, and a third layer including the loop material, wherein the mask assembly further comprises vent holes adapted to vent exhaled air from the mask, wherein the mask assembly further comprises at least one port in communication with an interior of the mask, and wherein the mask assembly further comprises an elbow connected to the mask, the elbow adapted to deliver pressurized gas to an interior of the mask.

17. The mask assembly of claim 16, wherein the mask further comprises a forehead support, and wherein the pair of elongated upper straps are configured to pass from the patient's forehead region to the back of the patient's head.

18. The mask assembly of claim 1, wherein the mask further comprises a forehead support, and wherein the pair of elongated upper straps are configured to pass from the patient's forehead region to the back of the patient's head.

19. The mask assembly of claim 1, wherein the pair of elongated upper straps and the pair of elongated lower straps are configured such that the elongated upper strap and the elongated lower strap on each lateral side of the headgear assembly are substantially parallel when the headgear assembly is laid flat.

20. A mask assembly suitable for the treatment of sleep disordered breathing, comprising:

a mask configured to provide pressurized air to a patient in the range of 3 to 20 cmH2O throughout the patient's respiratory cycle, the mask including a soft, face-contacting portion and a rigid shell;

a pair of upper headgear attachment points;

a pair of lower headgear attachment points; and a headgear assembly configured to hold the mask in position on the patient's face during treatment, comprising:

a top portion;

a bottom portion; and a pair of side portions, wherein the top portion, the bottom portion, and the pair of side portions define an opening that is arranged to receive the occiput of the patient's head in use;

a pair of elongated upper straps provided to opposing sides of the top portion and extending away from the top portion; and a pair of elongated lower straps provided to opposing sides of the bottom portion and extending away from the bottom portion, wherein in use each of the pair of elongated lower straps is angled downwardly relative to the bottom portion to displace a length of each of the pair of elongated lower straps downwardly with respect to the bottom portion such that a portion of each of the pair of elongated lower straps is lower than a lowest portion of a central region of the bottom portion, wherein each of the pair of elongated upper straps and each of the pair of elongated lower straps include a loop material positioned along an external surface thereof and a hook material configured to releasably attach to the loop material to attach the pair of elongated upper straps and the pair of elongated lower straps to the mask, wherein the pair of elongated upper straps are dimensioned to extend above the patient's ears, wherein the pair of elongated lower straps are dimensioned to extend below the patient's ears and across the patient's facial skin, wherein the loop material of each of the pair of elongated upper straps and each of the pair of elongated lower straps is sufficiently wider than the corresponding hook material such that when the hook material is attached to the loop material, in use, the loop material is configured to shield a user's skin from contact with the corresponding hook material, wherein a leading end of each of the pair of elongated upper straps is configured to pass through a corresponding one of the pair of upper headgear attachment points and be doubled-back on itself to attach the hook material to the loop material to secure the headgear assembly to the mask, wherein a leading end of each of the pair of elongated lower straps is configured to pass through a corresponding one of the pair of lower headgear attachment points and be doubled-back on itself to attach the hook material to the loop material to secure the headgear assembly to the mask, and wherein each of the pair of elongated lower straps is adapted to engage the patient's facial skin proximal to where the hook material is attached to the loop material.

21. The mask assembly of claim 20, wherein the pair of elongated upper straps and the pair of elongated lower straps consist essentially of four straps.

22. The mask assembly of claim 20, wherein the top portion is adapted to engage the crown of the patient's head.

23. The mask assembly of claim 20, wherein the bottom portion is dimensioned and configured so as to avoid engaging the patient's head below the occipital lobe in use.

24. The mask assembly of claim 20, wherein the top portion is dimensioned and configured to extend across the top of the patient's head from a first lateral side to a second lateral side of the patient's head in use.

25. The mask assembly of claim 20, wherein a thickness of each of the pair of elongated upper straps and the pair of elongated lower straps is approximately 2 mm.

26. The mask assembly of claim 20, wherein each of the pair of elongated upper straps and each of the pair of elongated lower straps is formed of a composite having a first layer to be positioned against the patient's head, a second, middle layer constructed from foam, and a third layer including the loop material.

27. The mask assembly of claim 20, further comprising vent holes adapted to vent exhaled air from the mask.

28. The mask assembly of claim 20, further comprising at least one port in communication with an interior of the mask.

29. The mask assembly of claim 20, further comprising an elbow connected to the mask, the elbow adapted to deliver pressurized gas to an interior of the mask.

30. The mask assembly of claim 20, wherein the mask is a full face mask.

31. The mask assembly of claim 20, wherein the mask is a nasal mask.

32. The mask assembly of claim 20, wherein the headgear assembly is formed without reinforcement or stiffeners.

33. The mask assembly of claim 20, wherein the pair of elongated lower straps are dimensioned such that in use a portion of the loop material that is attached to the hook material is located proximal to the patient's cheeks.

34. The mask assembly of claim 20, wherein the pair of elongated upper straps and the pair of elongated lower straps consist essentially of four straps, wherein the top portion is dimensioned and configured to extend across the top of the patient's head from a first lateral side to a second lateral side of the patient's head in use, wherein a thickness of each of the pair of elongated upper straps and the pair of elongated lower straps is approximately 2 mm, wherein the pair of elongated upper straps and the pair of elongated lower straps are configured such that the elongated upper strap and the elongated lower strap on each lateral side of the headgear assembly are substantially parallel when the headgear assembly is laid flat, wherein each of the pair of elongated upper straps and each of the pair of elongated lower straps is formed of a composite having a first layer to be positioned against the patient's head, a second, middle layer constructed from foam, and a third layer including the loop material, wherein the mask assembly further comprises vent holes adapted to vent exhaled air from the mask, wherein the mask assembly further comprises at least one port in communication with an interior of the mask, and wherein the mask assembly further comprises an elbow connected to the mask, the elbow adapted to deliver pressurized gas to an interior of the mask.

35. The mask assembly of claim 34, wherein the mask further comprises a forehead support, and wherein the pair of elongated upper straps are configured to pass from the patient's forehead region to the back of the patient's head.

36. The mask assembly of claim 20, wherein the mask further comprises a forehead support, and wherein the pair of elongated upper straps are configured to pass from the patient's forehead region to the back of the patient's head.

37. The mask assembly of claim 20, wherein the pair of elongated upper straps and the pair of elongated lower straps are configured such that the elongated upper strap and the elongated lower strap on each lateral side of the headgear assembly are substantially parallel when the headgear assembly is laid flat.

38. A mask assembly suitable for the treatment of sleep disordered breathing, comprising:
  a mask configured to provide pressurized air to a patient in the range of 3 to 20 cmH2O throughout the patient's respiratory cycle, the mask including a soft, face-contacting portion and a rigid shell;
  a pair of upper headgear attachment points;
  a pair of lower headgear attachment points; and
  a headgear assembly configured to hold the mask in position on the patient's face during treatment, comprising:
    a top portion;
    a bottom portion; and
    a pair of side portions,
    wherein the top portion, the bottom portion, and the pair of side portions define an opening that is arranged to receive the occiput of the patient's head in use;
    a pair of elongated upper straps provided to opposing sides of the top portion and extending away from the top portion;
    a pair of elongated lower straps provided to opposing sides of the bottom portion and extending away from the bottom portion,
  wherein each of the pair of elongated lower straps extend downwardly and away from the bottom portion such that in use a lower edge of the bottom portion is higher on the patient's head than a lower edge of each of the pair of elongated lower straps,
  wherein each of the pair of elongated upper straps and each of the pair of elongated lower straps include a loop material positioned along an external surface thereof and a hook material configured to releasably attach to the loop material to attach the pair of elongated upper straps and the pair of elongated lower straps to the mask, the hook material being narrower than the loop material of a corresponding strap,
  wherein the pair of elongated upper straps are dimensioned to extend above the patient's ears in use; and
  wherein the pair of elongated lower straps are dimensioned to extend below the patient's ears and across the patient's facial skin in use,
  wherein the loop material is configured to shield the patient's skin from contact with the hook material in use,
  wherein a leading end of each of the pair of elongated upper straps is configured to pass through a corresponding one of the pair of upper headgear attachment points and be doubled-back on itself to attach the hook material to the loop material to secure the headgear assembly to the mask,
  wherein a leading end of each of the pair of elongated lower straps is configured to pass through a corresponding one of the pair of lower headgear attachment points and be doubled-back on itself to attach the hook material to the loop material to secure the headgear assembly to the mask, and
  wherein each of the pair of elongated lower straps is adapted to engage the patient's facial skin proximal to where the hook material is attached to the loop material.

39. The mask assembly of claim 38, wherein the pair of elongated upper straps and the pair of elongated lower straps consist essentially of four straps.

40. The mask assembly of claim 38, wherein the top portion is adapted to engage the crown of the patient's head.

41. The mask assembly of claim 38, wherein the bottom portion is dimensioned and configured so as to avoid engaging the patient's head below the occipital lobe in use.

42. The mask assembly of claim 38, wherein the top portion is dimensioned and configured to extend across the top of the patient's head from a first lateral side to a second lateral side of the patient's head in use.

43. The mask assembly of claim 38, wherein a thickness of each of the pair of elongated upper straps and the pair of elongated lower straps is approximately 2 mm.

44. The mask assembly of claim 38, wherein each of the pair of elongated upper straps and each of the pair of elongated lower straps is formed of a composite having a first layer to be positioned against the patient's head, a second, middle layer constructed from foam, and a third layer including the loop material.

45. The mask assembly of claim 38, further comprising vent holes adapted to vent exhaled air from the mask.

46. The mask assembly of claim 38, further comprising at least one port in communication with an interior of the mask.

47. The mask assembly of claim 38, further comprising an elbow connected to the mask, the elbow adapted to deliver pressurized gas to an interior of the mask.

48. The mask assembly of claim 38, wherein the mask is a full face mask.

49. The mask assembly of claim 38, wherein the mask is a nasal mask.

50. The mask assembly of claim 38, wherein the headgear assembly is formed without reinforcement or stiffeners.

51. The mask assembly of claim 38, wherein the pair of elongated lower straps are dimensioned such that in use a portion of the loop material that is attached to the hook material is located proximal to the patient's cheeks.

52. The mask assembly of claim 38, wherein the pair of elongated upper straps and the pair of elongated lower straps consist essentially of four straps,
  wherein the top portion is dimensioned and configured to extend across the top of the patient's head from a first lateral side to a second lateral side of the patient's head in use,
  wherein a thickness of each of the pair of elongated upper straps and the pair of elongated lower straps is approximately 2 mm,
  wherein the pair of elongated upper straps and the pair of elongated lower straps are configured such that the elongated upper strap and the elongated lower strap on each lateral side of the headgear assembly are substantially parallel when the headgear assembly is laid flat,
  wherein each of the pair of elongated upper straps and each of the pair of elongated lower straps is formed of a composite having a first layer to be positioned against the patient's head, a second, middle layer constructed from foam, and a third layer including the loop material,
  wherein the mask assembly further comprises vent holes adapted to vent exhaled air from the mask,
  wherein the mask assembly further comprises at least one port in communication with an interior of the mask, and
  wherein the mask assembly further comprises an elbow connected to the mask, the elbow adapted to deliver pressurized gas to an interior of the mask.

53. The mask assembly of claim 52, wherein the mask further comprises a forehead support, and wherein the pair of elongated upper straps are configured to pass from the patient's forehead region to the back of the patient's head.

54. The mask assembly of claim 38, wherein the mask further comprises a forehead support, and wherein the pair of elongated upper straps are configured to pass from the patient's forehead region to the back of the patient's head.

55. The mask assembly of claim 38, wherein the pair of elongated upper straps and the pair of elongated lower straps are configured such that the elongated upper strap and the elongated lower strap on each lateral side of the headgear assembly are substantially parallel when the headgear assembly is laid flat.

* * * * *